United States Patent [19]
Gordon et al.

[11] Patent Number: 6,060,196
[45] Date of Patent: May 9, 2000

[54] STORAGE-STABLE ZINC ANODE BASED ELECTROCHEMICAL CELL

[75] Inventors: John H. Gordon, Salt Lake City; John J. McEvoy, Sandy; Strahinja K. Zecevic; Ashok V. Joshi, both of Salt Lake City, all of Utah

[73] Assignee: Ceramtec, Inc., Salt Lake City, Utah

[21] Appl. No.: 09/006,065

[22] Filed: Jan. 12, 1998

Related U.S. Application Data

[63] Continuation-in-part of application No. 08/539,998, Oct. 6, 1995, Pat. No. 5,707,499.

[51] Int. Cl.[7] .............................. H01M 4/42; C25B 9/00
[52] U.S. Cl. ......................... 429/229; 429/27; 429/101; 204/291; 204/283
[58] Field of Search ........................... 429/27, 101, 229; 204/291, 283

[56] References Cited

U.S. PATENT DOCUMENTS

| | | |
|---|---|---|
| 338,770 | 3/1886 | Otto . |
| 1,696,774 | 12/1928 | Martin . |
| 1,916,235 | 7/1933 | Ruben . |
| 2,680,449 | 6/1954 | Toulmin, Jr. . |
| 2,807,215 | 9/1957 | Hawxhurst . |
| 2,924,359 | 6/1960 | Beremand . |
| 2,979,897 | 4/1961 | Studhalter et al. . |
| 2,984,188 | 5/1961 | Tuckey et al. . |
| 3,115,280 | 12/1963 | Battista . |
| 3,425,697 | 2/1969 | Svagerko . |
| 3,430,731 | 3/1969 | Satzinger . |
| 3,602,214 | 8/1971 | London et al. . |
| 3,837,921 | 9/1974 | Henssen ........................... 136/86 A |
| 3,842,939 | 10/1974 | Satzinger . |
| 3,877,989 | 4/1975 | Waldman et al. . |
| 3,894,538 | 7/1975 | Richter . |
| 3,956,018 | 5/1976 | Kozawa . |
| 4,021,598 | 5/1977 | Naruishi et al. . |
| 4,023,648 | 5/1977 | Orlitzky et al. . |
| 4,038,467 | 7/1977 | Lippold et al. . |
| 4,054,726 | 10/1977 | Sauer et al. . |
| 4,068,049 | 1/1978 | Naruishi et al. . |
| 4,091,186 | 5/1978 | Ott et al. . |
| 4,136,236 | 1/1979 | Ruetschi et al. . |
| 4,139,683 | 2/1979 | Sauer et al. . |
| 4,144,382 | 3/1979 | Takeda et al. . |
| 4,189,526 | 2/1980 | Cretzmeyer et al. . |
| 4,192,914 | 3/1980 | Ruetschi . |
| 4,376,810 | 3/1983 | Takeda et al. . |
| 4,500,614 | 2/1985 | Nagamine et al. ..................... 429/206 |
| 4,617,242 | 10/1986 | Dopp . |
| 4,671,386 | 6/1987 | Orlitzky . |
| 4,735,876 | 4/1988 | Miura et al. . |
| 4,969,874 | 11/1990 | Michel et al. . |

(List continued on next page.)

FOREIGN PATENT DOCUMENTS

| | | |
|---|---|---|
| 961420 | 1/1975 | Canada . |
| 0 414 990 A1 | 3/1991 | European Pat. Off. . |
| 0 768 723 A1 | 4/1997 | European Pat. Off. . |
| 2139771 | 2/1973 | Germany . |
| 61-253764 | 11/1986 | Japan . |
| 62-08450 | 1/1987 | Japan . |
| 62-73565 | 4/1987 | Japan . |
| 62-243252 | 10/1987 | Japan . |
| 182457 | 3/1989 | Japan . |
| 2236973 | 9/1990 | Japan . |

Primary Examiner—Maria Nuzzolillo
Assistant Examiner—J. O'Malley
Attorney, Agent, or Firm—Factor & Partners

[57] ABSTRACT

A zinc alloy anode-based electrochemical cell, which generates gases and/or energy, is disclosed. The structure of the cell is such that a zinc alloy anode material is the integral part of housing and is in contact with an alkaline electrolyte containing minor amounts of corrosion inhibitors. The electrolyte which contains no zinc powder metal, may be in direct contact with the cathode thereby simplifying cell construction by elimination of a separator material. The cell is environmentally friendly, containing no mercury or cadmium or other toxic metals and is cost effective as it eliminates expensive amalgamated zinc powder and separator material.

28 Claims, 4 Drawing Sheets

U.S. PATENT DOCUMENTS

| | | |
|---|---|---|
| 4,971,669 | 11/1990 | Wrede et al. . |
| 5,112,465 | 5/1992 | Danielson . |
| 5,186,805 | 2/1993 | Gross et al. . |
| 5,242,565 | 9/1993 | Winsel ................................... 204/265 |
| 5,242,763 | 9/1993 | Konishi et al. . |
| 5,279,905 | 1/1994 | Mansfield, Jr. et al. . |
| 5,308,711 | 5/1994 | Passaniti et al. . |
| 5,318,861 | 6/1994 | Harats et al. ............................. 429/21 |
| 5,354,264 | 10/1994 | Bae et al. . |
| 5,378,562 | 1/1995 | Passaniti et al. . |
| 5,398,850 | 3/1995 | Sancoff et al. . |
| 5,398,851 | 3/1995 | Sancoff et al. . |
| 5,451,473 | 9/1995 | Oltmann et al. . |
| 5,486,431 | 1/1996 | Tuttle et al. . |
| 5,494,495 | 2/1996 | Tuttle . |
| 5,580,674 | 12/1996 | Tuttle et al. . |
| 5,582,930 | 12/1996 | Oltman et al. ............................ 429/27 |
| 5,603,157 | 2/1997 | Lake et al. . |

STORAGE-STABLE ZINC ANODE BASED ELECTROCHEMICAL CELL

RELATED APPLICATION

This application is a continuation-in-part of U.S. patent application Ser. No. 08/539,998 filed Oct. 6, 1995 (U.S. Pat. No. 5,707,499, Jan. 13, 1998) entitled "Storage-Stable Fluid Dispensing Device Using a Hydrogen Gas Generator". The specification of that prior patent application is hereby incorporated by this reference.

BACKGROUND OF THE INVENTION

1. Field of the Invention

The invention relates to galvanic cells of the zinc-anode type (e.g., zinc-air button cells) and in particular to miniature cells including those of gas and energy generation.

2. Background

Miniature button cells of various electrochemical systems such as $Zn-O_2$, $Zn-Ag_2O$, $Zn-HgO$, or $Zn-MnO_2$ are known for many years. Amongst them, $Zn-O_2$(air) cell has gained significant popularity because only the anode reaction material needs to be stored in the cell, whereas the cathode reaction material is oxygen, which is drawn from the surrounding air environment. Hence, the capacity and energy density of the zinc-air cell are determined by the stored amount of zinc metal and electrolyte solution in the cell.

The construction features of zinc-air button cells are quite similar to those of other commercially available zinc anode-based button cells. The zinc anode material is generally a loose, granulated powder mixed with gelled electrolyte to immobilize the composite and ensure adequate electrolyte contact with zinc particles. The two metal can halves, housing the cathode and anode active materials also act as the terminals, insulation between the two containers being provided by a plastic grommet. The top cap is of complex structure, pressed generally from a triclad metal sheet: outer surface is a protective layer of nickel over a core of steel. The inner surface that is in direct contact with the gelled zinc anode is high-purity copper or tin. The cathode sheet electrode is consolidated into the positive can, which is formed from nickel-plated steel having one or more holes to provide a path for oxygen to enter the cell and diffuse to the cathode catalyst sites. The cathode sheet structure includes catalyst layer, metallic mesh, hydrophobic membrane, diffusion membrane and air-distribution layer. The catalyst layer contains carbon, usually blended with oxides of manganese or silver. It is made hydrophobic by addition of finely dispersed polytetrafluoroethylene ("PTFE") particles. The metallic mesh provides structural support and acts as the current collector. The hydrophobic membrane maintains the gas-permeable waterproof boundary between the air and the cell's electrolyte. The diffusion membrane regulates gas diffusion rates. Finally, the air distribution layer distributes oxygen evenly over the cathode surface. It should be pointed out that one of the main construction features of commercially available button zinc-air cells is the presence of a separator to keep the anode and cathode separated. The use of separator is required as a consequence of the fact that the zinc anode is in powdered gelled form and therefore it must be separated from a direct electrical contact with the cathode.

Another fact related to the construction of button type zinc cells should also be pointed out. The zinc anode is in the form of gelled powder not only in zinc-air button cells (see, e.g., U.S. Pat. Nos. 4,054,726, 4,189,526, 5,242,763, 5,279,905, 5,308,711, and 5,451,473), but also in other types of zinc anode-based button cells such as zinc-silver oxide (see, e.g., U.S. Pat. Nos. 4,021,598, 4,038,467, 4,068,049, 4,139,683, and 4,144,382) or zinc-carbon alkaline cells (U.S. Pat. Nos. 3,956,018, 4,091,186, 4,136,236, 4,192,914, 4,376,810, 4,617,142, 4,735,876, and 5,378,562). There are also several foreign patents in which zinc anode is also in powdered form (Japanese Patent publications 2236973, 6208450, 6273565, 61253764, and 62243252, and European Patent publications 768,723 and 414,990). In addition, the zinc powder is usually amalgamated to reduce gassing. Since mercury can be environmentally deleterious, significant efforts have been made to reduce the quantity of mercury in such cells. The most common way to reduce the gassing rate is by alloying the zinc powder with metals such as lead, cadmium, indium, bismuth, gallium, aluminum, tin etc., or adding oxides and/or hydroxides of these metals into the gelled powder mix.

In the absence of oxygen (or when a sintered PTFE membrane is utilized as the gas diffusion membrane), the zinc-air cell functions as a hydrogen gas generating cell as shown by Winsel in U.S. Pat. No. 5,242,565. In Winsel's button cell, the zinc anode is also in the form of gelled powder and the cell contains a separator. However, regardless of whether the cell is to be used as a current source or a gas generator, it is preferable for the cell to be of simple construction, to have fewer components, ease manufacturing and to be environmentally friendly.

BRIEF SUMMARY OF THE INVENTION

The invention includes a novel button-type zinc based electrochemical cell of much simpler construction that utilizes a zinc strip cap anode and contains neither separator nor a gelled zinc powdered anode. The invention also provides for a long-life energy cell that occupies a minimum amount of space. The invention also provides an electrochemical cell (gas generating or energy producing cell) that is free from mercury, or cadmium, which poses a significantly reduced hazard to the environment. The invention also can provide a storage battery suitable for gas generating cell applications, which is substantially unaffected by changes in the ambient relative humidity.

This invention relates to a zinc-anode-based electrochemical button cell, which generates gasses or energy or mixture thereof. The cell is of a much simpler construction than that of commercially available zinc anode-based button cells, because a zinc anode material is not in the form of gelled metal powder. Instead of zinc powder, a zinc alloy cap forming a cup-shaped interior cavity of the cell, is used as the anode of the cell. The zinc alloy is of a high purity with iron levels preferably less than 10 ppm. Other impurities to avoid include, nickel, cobalt, tungsten, molybdenum, and germanium. Thus, the zinc anode material is an integral part of the cell housing, and is in contact with an alkaline electrolyte, which is typically an aqueous solution of sodium hydroxide. The absence of zinc powder in the electrolyte eliminates the need for a separator that further simplifies the cell construction and lowers its cost. The zinc anode cap is a zinc alloy containing at least one metal from the group consisting of lead, indium, gallium, bismuth and combinations and equivalents thereof. The zinc cap has a copper, tin, or stainless steel clad outer layer to protect the zinc anode from atmospheric corrosion.

The electrolyte contains small amounts of zinc oxide, indium oxide, and alkali polyacrylate, compounds which act as corrosion inhibitors, and thus suppress gassing of the zinc anode. Since zinc powder is omitted from the electrolyte, more electrolyte can be utilized, resulting in a longer cell life time.

The cathode, made up of a mixture of metal oxides, active carbon powder, and PTFE finely dispersed particles, is substantially gas permeable and partially hydrophobic. The cathode is pressed into metal screen which acts as the current collector, and placed at the bottom of a nickel-plated stainless steel can over a sheet of fluoropolymer acting as water evaporation barrier. The stainless steel has at least one opening to permit gas to pass into the cell or to escape from the cell depending on the operation mode of the cell. When the cell is used in its gas generating mode, a sintered PTFE membrane is placed between the hydrophobic barrier and the gas passage to prevent incoming of air into the cell.

The zinc cap anode and stainless steel can and gas permeable cathode are electrically isolated with an insulating grommet.

In brief, the present invention offers a zinc anode-based button cell of a simple construction having less parts, containing no mercury or cadmium, and being less expensive than commercially available zinc anode-based button cells.

DETAILED DESCRIPTION OF THE INVENTION

Figure 1:
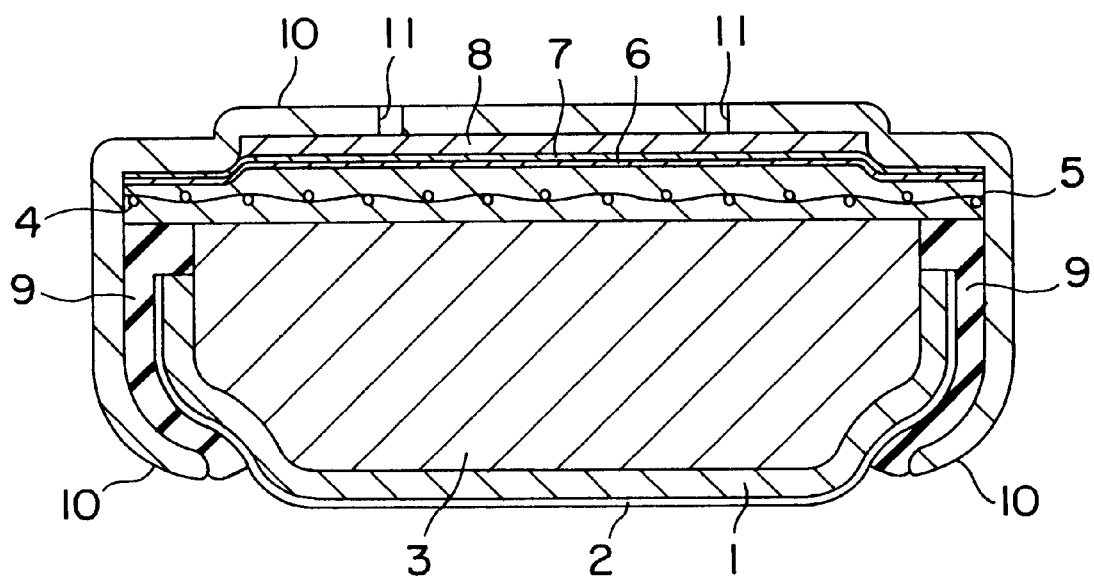
FIG. 1 shows a cross-sectional view of one embodiment of a button cell according to the present invention, wherein the electrochemical cell is a hydrogen gas generating cell comprising a gas-evolving cathode and semipermeable membranes permeable to hydrogen and impermeable to moisture and air.

A preferred embodiment of the invention is shown in FIG. 1, which is a button cell type of zinc anode-based electrochemical cell. It comprises a zinc alloy cap 1 with a copper, tin or stainless steel clad outer layer 2 forming a substantially cup-shaped interior cavity and acting as the anode of the cell. The zinc alloy contains zinc metal with minimal amounts of impurities and includes indium, lead, gallium, bismuth or combinations thereof as alloying elements. The interior surface of the cap is zinc alloy in direct contact with the electrolyte 3.

The electrolyte 3 is an aqueous solution of one of the alkaline hydroxides such as NaOH, KOH, LiOH or mixtures thereof, containing small amounts of zinc oxide, indium oxide and gelling agent, which suppress gassing. The gelling agent is preferably either a mixture of sodium polyacrylate, acrylic acid and amorphous hydrophobic silicon dioxide, or sodium carboxymethyl cellulose.

Since the aqueous alkaline electrolyte does not contain any gelled zinc powder, it can be in direct contact with the cathode 4. The cathode 4 is of the "sheet-type" and preferably comprises activated carbon as the conductive material, metal oxide catalyst for the electrochemical reactions, and PTFE dispersed throughout as a hydrophobic binder. Electrocatalyst suitable for the cathode reaction when the electrochemical cell is a hydrogen gas-generating cell, includes Raney nickel or high surface area nickel metal powder. When the electrochemical cell is an oxygen-consuming cell, suitable cathode catalysts involve high surface area powders of oxides of manganese, silver or mixtures thereof. The conductive material in the cathode 4 can be made up of carbon, graphite, silver or mixtures thereof. This composite matrix material is pressed onto either nickel or nickel-plated steel mesh material 5, and then pressed into a sheet of fluoropolymer 6 which is hydrophobic in nature and acts as a moisture barrier. Other hydrophobic materials are also suitable for use with this type of electrochemical cell and are known in the art.

In accordance with the present invention, there is interposed a membrane layer 7 which limits air diffusion passing through the cathode (in a gas generating mode). Unsintered PTFE membranes filled with carbon and sintered PTFE films are likewise acceptable for this purpose. Optionally, a porous diffusion layer 8 such as filter paper is positioned adjacent to the interior of the cathode can or casing 10, although it is not a necessary element. A grommet 9 (preferably of nylon) electrically isolates the anode cap 2 from the cathode 4 and from the cathode can 10. The can 10 is crimped around the grommet cap assembly forming a seal. The cathode can 10 is comprised of nickel-plated stainless steel, and is in direct electrical contact with the cathode mesh 5. The can 10 has at least one aperture 11 to permit passage of gasses in or out of the cell.

One significant advantage of this invention is that it eliminates the separator used in the prior art, thus requiring fewer components. Another advantage of this invention is that it eliminates the presence of powdered zinc material in the electrolyte, resulting in a higher capacity of the cell because the cell can now hold more electrolyte. It is, however, important to point out that alkaline electrolyte in the present cell should contain corrosion inhibitors to reduce the self-discharge rate, and, consequently, to extend the storage life of the cell. For example, the addition of zinc oxide, indium oxide, gallium oxide and the like are desirable. In addition, gelling agent may be added to the electrolyte not only to reduce the incidence of leakage, but also to reduce the corrosion rate of zinc. The inclusion of indium oxide $In_2O_3$ in the electrolyte has a particularly beneficial effect on reducing gassing and corrosion.

Generally, the self-discharge rate is inversely related to the quantity of oxide in the electrolyte. However, the presence of about 300 ppm of indium oxide is optimal, and the inclusion of additional indium oxide provides improvement, but only marginally. Generally about 25 ppm to about 300 ppm indium oxide is preferred in the electrolyte with especially good results being obtained above about 50 ppm indium oxide.

Figure 2:
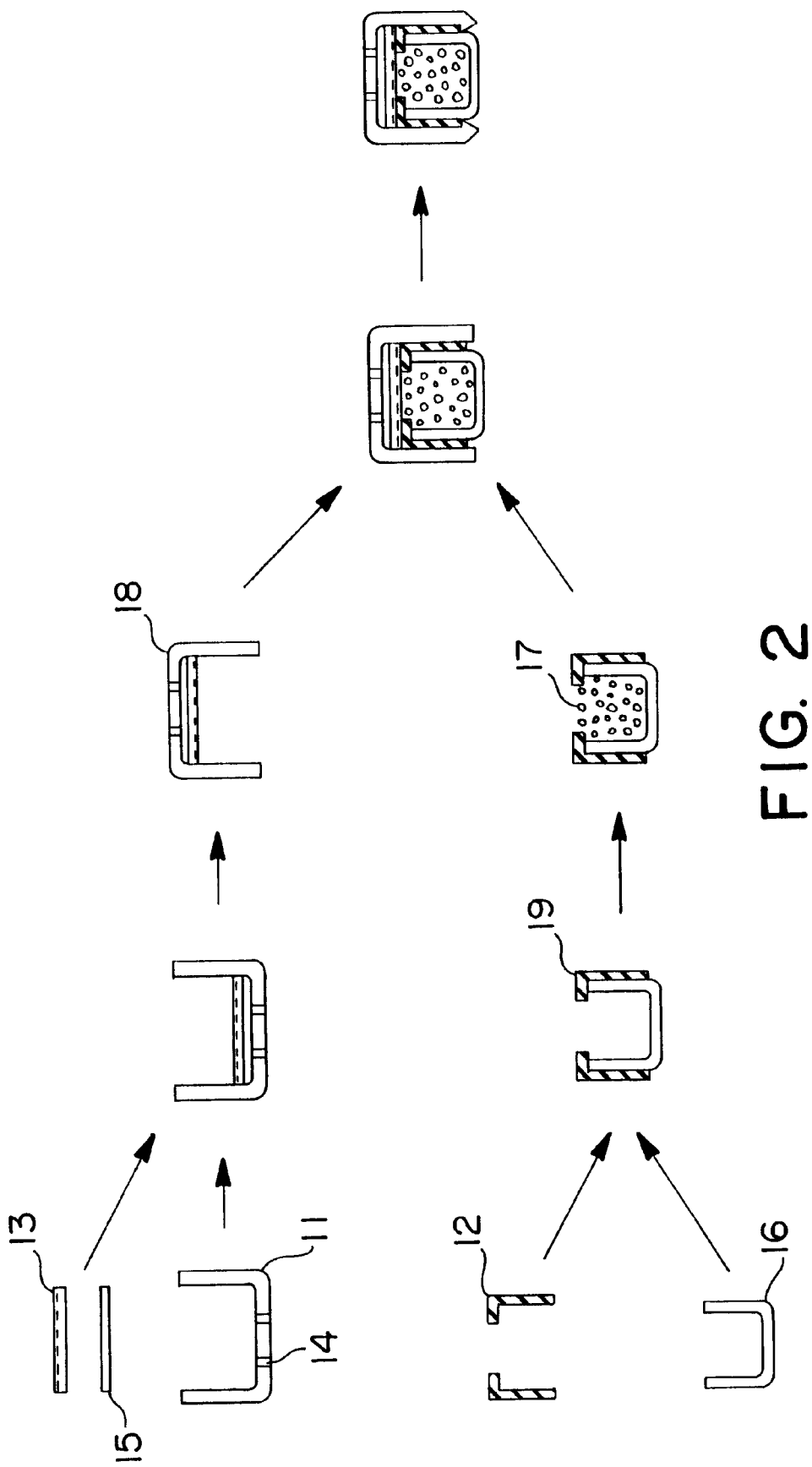
FIG. 2 is diagrammatic plan view of steps of a method of producing the cell in accordance with the invention.

The following example illustrates a method of producing the cell, and is shown in FIG. 2. The main feature of the method is its great simplicity. An air electrode subassembly, comprising the cathode 13 and water-impermeable gas permeable membrane 15, is placed at the bottom of an outer nickel-plated steel can 11, thus forming a cathode subassembly 18. At the same time, a nylon grommet 12 is firmly placed around a zinc cap 16, thus forming the anode subassembly 19. The anode subassembly is then filled with gelled electrolyte 17. The filled anode subassembly is then covered with the cathode subassembly 18, and finally crimped (or otherwise associated with one another) to form the button veil.

Figure 3:
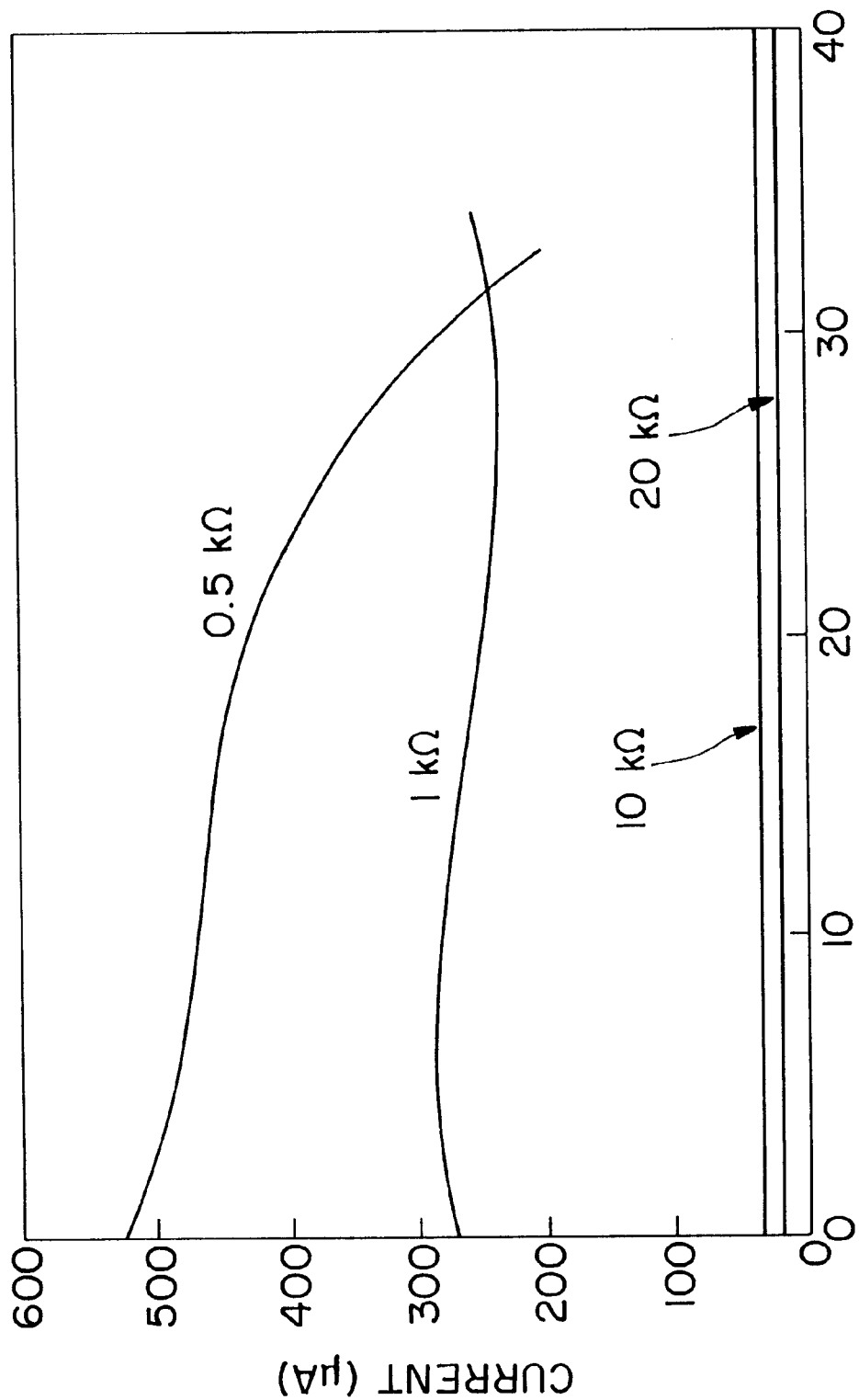
FIG. 3 shows typical discharge curves of button gas generating cells of the present invention under different loads 0.5 k$\Omega$, 1 k$\Omega$, 10 k$\Omega$, and 20 k$\Omega$.

FIG. 3 is a graph of current versus time for the zinc anode-based hydrogen gas-generating cells under different loads, and illustrating one example of cell characteristics capable of being achieved with the present invention. The cells were constructed as shown in FIG. 1, and had a sintered PTFE gas diffusion film. As can be seen, the slopes of discharge curves depend on the cell discharge rate being very low at a low discharge rate. These results indicate a very stable cell operation under the specified conditions.

Figure 4:
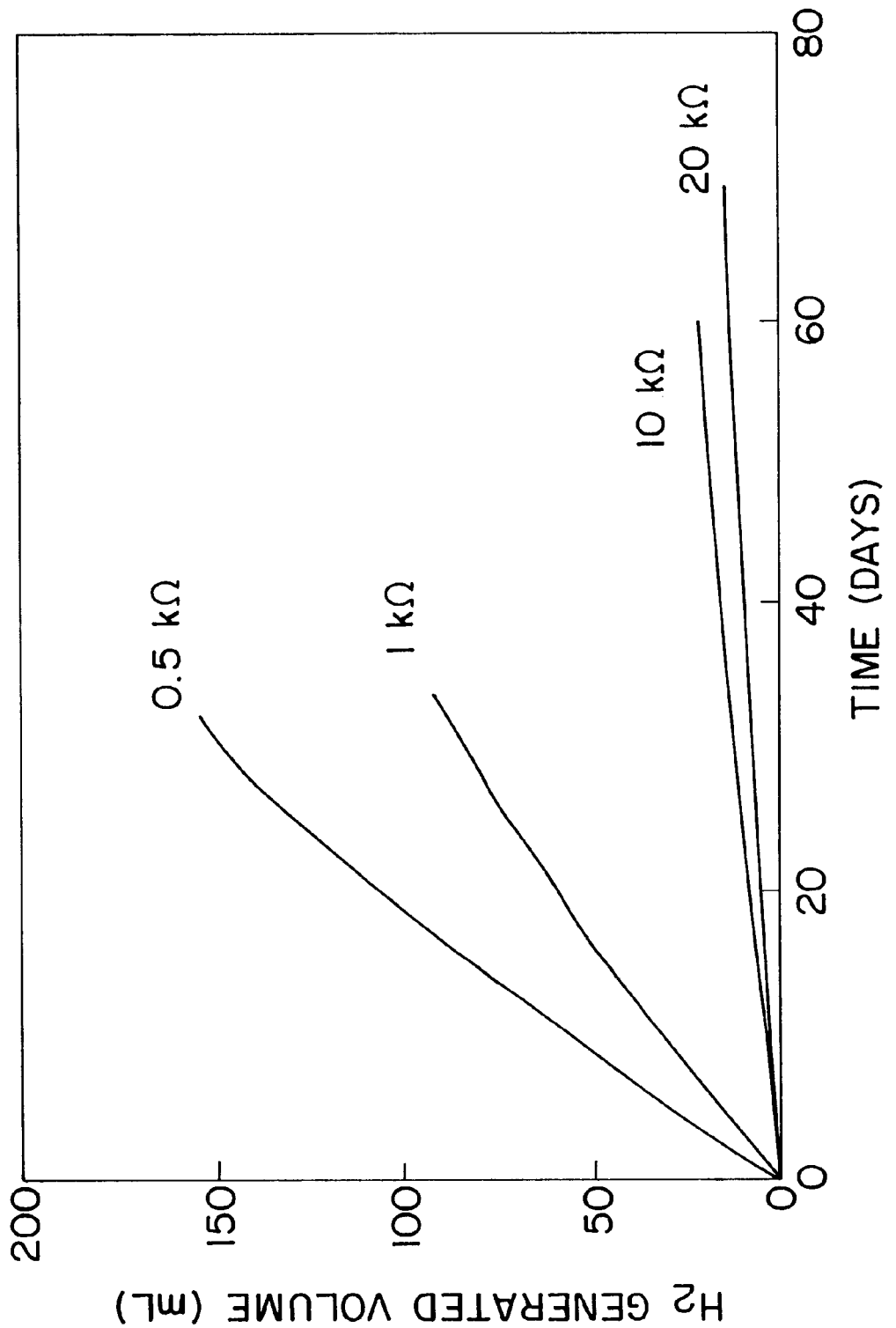
FIG. 4 shows typical hydrogen volume delivery curves of button gas generating cell of the present invention under different loads 0.5 k$\Omega$, 1 k$\Omega$, 10 k$\Omega$, and 20 k$\Omega$.

FIG. 4 depicts a plot of gas generation versus time at different loads. The cells were constructed as shown in FIG. 1 and had a sintered PTFE gas diffusion film.

Although the invention has been described with reference to certain particular embodiments and examples, these have been provided for illustrative purposes only, and the scope of the invention is to be determined by the appended claims.

What is claimed is:

1. A galvanic cell comprising:
   a zinc alloy anode formed into a cap, said cap forming a substantially cup-shaped interior cavity,
   an alkaline electrolyte containing alkali metal hydroxide, zinc oxide, and corrosion inhibitors in aqueous solution in contact with and substantially filling said anode alloy cup-shaped interior cavity,
   a cathode comprising a mixture of metal oxides and conductive materials, said cathode being in direct contact with said alkaline electrolyte in the absence of a separator, said cathode structured to be substantially gas permeable and partially hydrophobic, at least on a side opposite that of the electrolyte,
   an insulating grommet electrically isolating said zinc alloy cap from said gas permeable cathode,
   an outer can, structurally in contact with and holding the grommet and the cathode in place, said outer can having at least one aperture through which gas may enter in or vent from the galvanic cell wherein said gas may be electrically discharged or produced by electrically interconnecting said zinc alloy cap and said outer can, and
   a gas permeable hydrophobic membrane between said cathode and said gas aperture,
     wherein the galvanic cell is constructed to generate gas or energy or mixture thereof and wherein the galvanic cell is active when an electrical connection is made between the cap and the can.

2. The galvanic cell of claim 1 wherein the zinc alloy consists essentially of zinc metal together with alloying elements selected from the group consisting of indium, lead, gallium, bismuth or combinations thereof.

3. The galvanic cell of claim 1 wherein the cathode is a sheet comprising activated carbon and fluoropolymer composite matrix pressed into either nickel or nickel-plated steel screen and where said screen is pressed into a film of microporous fluoropolymer.

4. The galvanic cell of claim 1 wherein said gas permeable hydrophobic membrane is polytetrafluoroethylene.

5. The galvanic cell of claim 1 wherein oxygen is consumed at the cathode during discharge of the galvanic cell.

6. The galvanic cell of claim 1 wherein hydrogen is released at the cathode during discharge of the galvanic cell.

7. The galvanic cell of claim 1 wherein the alkali metals hydroxide contains NaOH, LiOH, KOH or mixtures thereof.

8. The galvanic cell of claim 1 wherein the electrochemical cell is a hydrogen gas generating cell comprising a gas-evolving cathode composed of at least hydrogen permeable hydrophobic membrane along with a current collector and hydrogen generating electrocatalyst.

9. The galvanic cell according to claim 8, wherein said electrocatalyst includes Raney nickel or nickel metal powder.

10. The galvanic cell of claim 8 wherein the hydrogen permeable hydrophobic membrane includes sintered nonporous PTFE sheet.

11. The galvanic cell of claim 1 wherein the electrochemical cell is an oxygen consuming cell comprising an oxygen permeable cathode comprised of at least an oxygen permeable hydrophobic membrane, along with a current collector and oxygen reduction electrocatalyst.

12. The galvanic cell of claim 11, wherein said electrocatalyst containing oxides of manganese, silver and mixtures thereof.

13. The galvanic cell of claim 11 wherein the oxygen permeable hydrophobic membrane includes PTFE sheet.

14. The galvanic cell of claim 1 wherein said zinc alloy cap is clad or coated on the exterior side with a corrosion resistant metal consisting of copper, tin, or stainless steel.

15. The galvanic cell of claim 1 wherein said corrosion inhibitors include indium oxide.

16. The galvanic cell of claim 1 wherein said corrosion inhibitors include alkali polyacrylate.

17. A method of producing a galvanic cell according to claim 1, said method comprising:
   placing a gas permeable electrode subassembly comprising a cathode and gas permeable hydrophobic membrane at the bottom of an outer nickel-plated steel can, thus forming a cathode subassembly,
   placing a grommet around a zinc cap forming an anode subassembly and then filling the anode subassembly with alkaline electrolyte,
   interacting the cathode subassembly with the electrolyte-filled anode subassembly in the absence of a separator, and
   crimping the cathode subassembly about the electrolyte-filled anode subassembly to form the galvanic cell.

18. The method of producing a galvanic cell according to claim 17 wherein said zinc cap is clad or coated on the exterior side with a corrosion resistant metal consisting of copper, tin, or stainless steel.

19. The method of producing a galvanic cell according to claim 17 wherein the alkaline electrolyte contains alkali metal hydroxide, zinc oxide, and corrosion inhibitors in aqueous solution in contact with and substantially filling said anode alloy cup-shaped interior cavity.

20. The method of producing a galvanic cell according to claim 17 wherein a cathode is made up of mixture of metal oxides and conductive materials, said cathode being in direct contact with said electrolyte, said cathode structured to be substantially gas permeable and partially hydrophobic, at least on the side opposite the electrolyte.

21. The method of producing galvanic cell of claim 17 wherein the grommet electrically isolates said zinc alloy cap from said gas permeable cathode.

22. The method of producing the galvanic cell according to claim 17 wherein an outer can is structurally in contact with and holds the grommet and the cathode in place, said outer can having at least one aperture through which gas may enter in or vent from the cell wherein said gas may be electrically discharged or produced by electrically interconnecting said zinc alloy cap and said outer can.

23. The method of producing a galvanic cell according to claim 17 wherein a gas permeable hydrophobic membrane is placed between said cathode and said gas aperture.

24. The method of producing a galvanic cell according to claim 17 wherein the galvanic cell is constructed to generate gas or energy or mixture thereof.

25. A galvanic cell comprising:

a zinc alloy anode, shaped to form a portion of an interior cavity;

an alkaline electrolyte within said interior cavity;

a cathode configured for direct contact with said electrolyte in the absence of a separator, said cathode structured to be gas permeable and at least partly hydrophobic, at least on the side opposite the electrolyte;

a grommet between at least a portion of said anode and a portion of said cathode;

an outer shell, having at least one aperture through which gas may pass; and a gas permeable hydrophobic membrane between said cathode and said aperture.

26. The galvanic cell of claim 25 wherein said shell is electrically connected to said cathode.

27. The galvanic cell of claim 26, wherein said cell is activated by a connection of said anode to said shell.

28. A galvanic cell, comprising:

a zinc alloy anode, shaped to form a portion of an interior cavity;

an alkaline electrolyte within said interior cavity void of anodic material;

a cathode configured for direct contact with said electrolyte without a separator, said cathode structured to be gas permeable and at least partly hydrophobic, at least on the side opposite the electrolyte;

a grommet between at least a portion of said anode and a portion of said cathode;

an outer shell, having at least one aperture through which gas may pass; and a gas permeable hydrophobic membrane between said cathode and said aperture.

* * * * *

UNITED STATES PATENT AND TRADEMARK OFFICE
CERTIFICATE OF CORRECTION

PATENT NO. : 6,060,196
DATED : May 9, 2000
INVENTOR(S) : Gordon et al.

It is certified that error appears in the above-identified patent and that said Letters Patent is hereby corrected as shown below:

Column 2,
Line 67, After polyacrylate, delete "compounds which" and insert instead -- which compounds --.

Column 4,
Line 7, After silver delete "or" and insert instead -- and --.

Column 5,
Line 5, Delete "bad" and insert -- had --.

Signed and Sealed this

Fourteenth Day of August, 2001

*Attest:*

NICHOLAS P. GODICI
*Attesting Officer*      *Acting Director of the United States Patent and Trademark Office*